US012239294B2

(12) United States Patent
DiCarlo et al.

(10) Patent No.: US 12,239,294 B2
(45) Date of Patent: Mar. 4, 2025

(54) ILLUMINATION CORRECTED NEAR-INFRARED (NIR) IMAGING FOR IMAGE GUIDED SURGERY

(71) Applicant: INTUITIVE SURGICAL OPERATIONS, INC., Sunnyvale, CA (US)

(72) Inventors: Jeffrey M. DiCarlo, Austin, TX (US); Ian E. McDowall, Woodside, CA (US); Max J. Trejo, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 875 days.

(21) Appl. No.: 17/311,002

(22) PCT Filed: Dec. 3, 2019

(86) PCT No.: PCT/US2019/064142
§ 371 (c)(1),
(2) Date: Jun. 4, 2021

(87) PCT Pub. No.: WO2020/117744
PCT Pub. Date: Jun. 11, 2020

(65) Prior Publication Data
US 2022/0015857 A1   Jan. 20, 2022

Related U.S. Application Data

(60) Provisional application No. 62/775,451, filed on Dec. 5, 2018.

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00009* (2013.01); *A61B 1/046* (2022.02);
(Continued)

(58) Field of Classification Search
CPC ..... A61B 1/043; A61B 1/00009; A61B 1/046; A61B 5/0071; A61B 90/37;
(Continued)

(56) References Cited

U.S. PATENT DOCUMENTS 7,102,142 B2  9/2006 Sendai
8,654,185 B2  2/2014 Ono
(Continued)

FOREIGN PATENT DOCUMENTS

CN  107155302 A  9/2017
CN  107851176 A  3/2018
(Continued)

OTHER PUBLICATIONS

International Preliminary Report on Patentability for Application No. PCT/US2019/064142, mailed on Jun. 17, 2021, 10 pages.
(Continued)

*Primary Examiner* — Bo Joseph Peng

(57) ABSTRACT

Technology described herein can be embodied in a method of displaying a visual representation of a portion of a surgical scene. The method includes receiving data representing information captured using a first sensor of a camera associated with a surgical device, the information being indicative of a first quantity representing an amount of fluorescence emitted from the portion of the surgical scene. The method also includes obtaining information indicative of a second quantity representing an amount of excitation signal causing the fluorescence to be emitted from the portion of the surgical scene, and generating a normalized fluorescence signal as a function of the first quantity and the
(Continued)

second quantity. The method further includes generating the visual representation of the portion of the surgical scene based on the normalized fluorescence signal, and presenting the visual representation on a display device associated with the surgical device.

10 Claims, 6 Drawing Sheets

(51) Int. Cl.
*A61B 5/00* (2006.01)
*A61B 90/00* (2016.01)

(52) U.S. Cl.
CPC ............ *A61B 5/0071* (2013.01); *A61B 90/37* (2016.02); *A61B 2090/371* (2016.02); *A61B 2090/373* (2016.02)

(58) Field of Classification Search
CPC ........ A61B 2090/371; A61B 2090/373; A61B 1/00045; A61B 1/3132
See application file for complete search history.

(56) References Cited

U.S. PATENT DOCUMENTS

| | | | |
|---|---|---|---|
| 9,182,347 B2 | 11/2015 | Ishihara | |
| 10,634,615 B2 | 4/2020 | Rizo et al. | |
| 2003/0218137 A1* | 11/2003 | Sendai | A61B 5/0086 250/461.1 |
| 2004/0148141 A1 | 7/2004 | Tsujita et al. | |
| 2004/0245350 A1* | 12/2004 | Zeng | A61B 1/042 236/77 |
| 2006/0184043 A1* | 8/2006 | Tromberg | A61B 5/0071 600/476 |
| 2009/0270678 A1* | 10/2009 | Scott | A61B 1/000096 600/109 |
| 2012/0323072 A1 | 12/2012 | Ishihara | |
| 2012/0328175 A1 | 12/2012 | Watanabe | |
| 2014/0184769 A1 | 7/2014 | Ishihara et al. | |
| 2018/0238901 A1* | 8/2018 | Schaaf | G01N 33/542 |

FOREIGN PATENT DOCUMENTS

| | | |
|---|---|---|
| EP | 3050485 A1 | 8/2016 |
| JP | H10108831 A | 4/1998 |
| JP | 2001224549 A | 8/2001 |
| JP | 2003339623 A | 12/2003 |
| JP | 2004008230 A | 1/2004 |
| JP | 2008229025 A | 10/2008 |
| JP | 2009542415 A | 12/2009 |
| JP | 2011194164 A | 10/2011 |
| JP | 2013056001 A | 3/2013 |
| WO | WO-2008008231 A2 | 1/2008 |
| WO | WO-2011111619 A1 | 9/2011 |
| WO | WO-2015023990 A1 | 2/2015 |

OTHER PUBLICATIONS

International Search Report and Written Opinion for Application No. PCT/US2019/064142, mailed Mar. 17, 2020, 18 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

ILLUMINATION CORRECTED NEAR-INFRARED (NIR) IMAGING FOR IMAGE GUIDED SURGERY

CROSS-REFERENCE TO RELATED APPLICATIONS

This application is a U.S. National Stage Application under 35 U.S.C. § 371 and claims the benefit of International Application No. PCT/US2019/064142 titled "Illumination Corrected Near-Infrared (NIR) Imaging for Image Guided Surgery," filed on Dec. 3, 2019, which claims the benefit of U.S. Provisional Application No. 62/775,451 titled "Illumination Corrected Near-Infrared (NIR) Imaging for Image Guided Surgery," filed on Dec. 5, 2018. The disclosures of the foregoing applications are incorporated herein by reference in their entirety.

TECHNICAL FIELD

This disclosure relates to near-infrared (NIR) imaging used in endoscopic surgical systems.

BACKGROUND

Minimally invasive surgical systems are being developed to reduce the trauma experienced by patients undergoing surgical interventions. These systems require only small incisions and surgeons use stick like cameras and instruments to perform the procedure. In addition to reducing trauma, teleoperated systems of this type increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site through a display device. Based on visual feedback received through the display device, the surgeon performs the surgical procedures on the patient by manipulating master control input devices, which in turn control the motion of tele-robotic instruments.

SUMMARY

In one aspect, this document features a method of displaying a visual representation of a portion of a surgical scene. The method includes receiving data representing information captured using a first sensor of a camera associated with a surgical device, the information being indicative of a first quantity representing an amount of fluorescence emitted from the portion of the surgical scene. The method also includes obtaining information indicative of a second quantity representing an amount of excitation signal causing the fluorescence to be emitted from the portion of the surgical scene, and generating, by one or more processing devices, a normalized fluorescence signal as a function of the first quantity and the second quantity. The method further includes generating the visual representation of the portion of the surgical scene based on the normalized fluorescence signal, and presenting the visual representation of the portion of the surgical scene on a display device associated with the surgical device.

In another aspect, this document features an imaging system that includes a first image sensor and a rendering engine. The first image sensor is configured to sense information indicative of a first quantity representing an amount of fluorescence emitted from a portion of a surgical scene. The rendering engine includes one or more processing devices, and is configured to obtain information indicative of a second quantity representing an amount of excitation signal causing the fluorescence to be emitted from the portion of the surgical scene, generate a normalized fluorescence signal as a function of the first quantity and the second quantity, and generate a visual representation of the portion of the surgical scene based on the normalized fluorescence signal. The system also includes a display device configured to present the visual representation.

In another aspect, this document features one or more non-transitory machine-readable storage devices having encoded thereon instructions for causing one or more processing devices to perform various operations. The operations include receiving data representing information captured using a first sensor of a camera associated with a surgical device. The information is indicative of a first quantity representing an amount of fluorescence emitted from a portion of a surgical scene. The operations also include obtaining information indicative of a second quantity representing an amount of excitation signal causing the fluorescence to be emitted from the portion of the surgical scene, and generating a normalized fluorescence signal as a function of the first quantity and the second quantity. The operations further include generating a visual representation of the portion of the surgical scene based on the normalized fluorescence signal, and causing a presentation of the visual representation of the portion of the surgical scene on a display device associated with the surgical device.

Implementations of the above aspects can include one or more of the following features.

Obtaining the information indicative of the second quantity can include receiving a portion of the excitation signal as reflected from the portion of the surgical scene, capturing the portion of the excitation signal using a second sensor, and determining the second quantity based on an output signal from the second sensor. Each of the first sensor and the second sensor can be a near-infrared (NIR) sensor. Capturing the portion of the excitation signal can include changing a direction of propagation of the portion of the excitation signal towards the second sensor. The direction of propagation can be changed using a reflective element disposed at an angle with respect to the direction of propagation. Obtaining the information indicative of the second quantity can include accessing a depth map associated with a source of the excitation signal, wherein the depth map provides information on intensity variations of the excitation signal as a function of spatial separation from the source. Obtaining the information indicative of the second quantity can also include receiving data representing information about a spatial separation between the portion of the surgical scene and the source of the excitation signal, and determining the second quantity based on (i) the spatial separation between the portion of the surgical scene and the source, and (ii) the depth map. The data representing information about the spatial separation can be received from a third sensor. The information about the spatial separation between the portion of the surgical scene and the source can include at least one of (i) an angle between the portion of the surgical scene and the source, and (ii) a distance between the portion of the surgical scene and the source. Presenting the visual representation can include receiving user-input on a threshold condition associated with the normalized fluorescence signal, determining regions where the normalized fluorescence signal satisfies the threshold condition, and generating the visual representation such that the visual representation includes identification of the regions where the normalized fluorescence signal satisfies the threshold condition. In some cases, user input can be received responsive to presenting the visual representation of the surgical scene on the display device, wherein the user input pertains to operating the surgical device at the surgical scene. The camera can be disposed in the surgical device. The function of the first quantity and the second quantity can include a ratio of the first quantity to the second quantity.

Some or all of the embodiments described herein may provide one or more of the following advantages. By normalizing pixel values of an NIR image with respect to values representing an amount of excitation energy incident on the corresponding portions, undesirable effects due to illumination variations across the image may be substantially mitigated. This in turn may allow for the detected intensity of NIR fluorescence to be independent of endoscope position. Such positional independence can allow for a more accurate determination of an actual quantity of a dye (e.g., indocyanine green (ICG)) in a particular tissue type, and may make it easier for a surgeon to locate the margins of tissue regions afflicted with a disease such as cancer.

DETAILED DESCRIPTION

Figure 2:
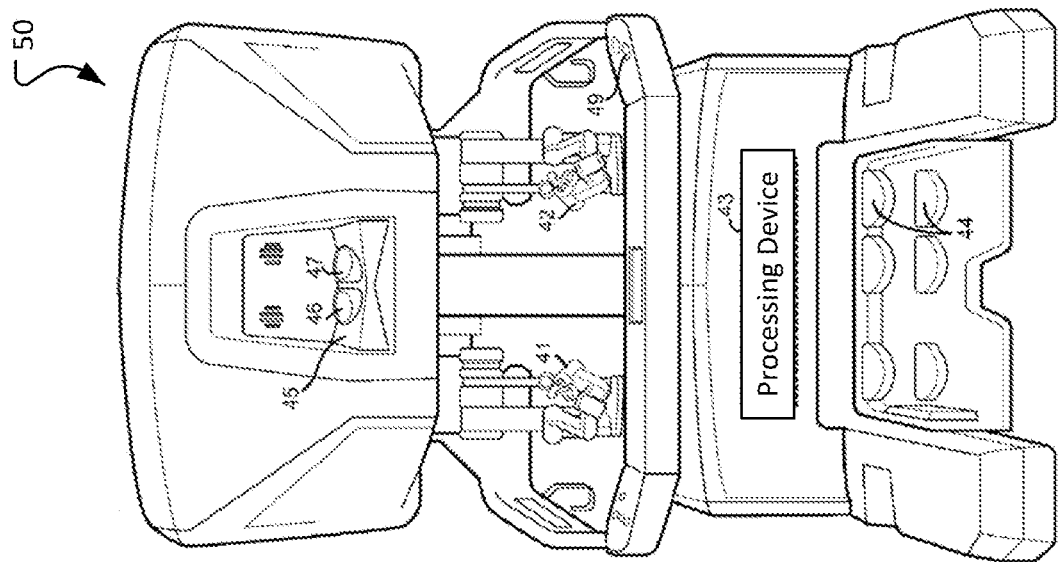
FIG. 2 is a front view of an example surgeon console of a computer-assisted tele-operated surgery system.

This document describes near-infrared (NIR) imaging technology in which the detected fluorescence signal for various portions of an image is normalized with respect to a measure of excitation energy estimated to be incident on tissues corresponding such portions. The measure of excitation energy may be determined in multiple ways. In some cases, the measure of excitation energy is derived based on an output of a sensor configured to sense an amount of excitation energy reflected from the tissue. In some cases, the measure of excitation energy can be computed using a theoretical or empirical model that represents the physics of the electromagnetic radiation directed from the endoscope towards the tissue. The normalized NIR images generated using the technology described herein accounts for variations in fluorescence signal due to the variations in the amount of incident excitation energy (attributable to, for example, different distances, orientations with respect to the energy source), and may provide a more accurate representation of the underlying fluorescence. In some cases, this in turn may be used more reliably to determine the true amount of dye (e.g., indocyanine green (ICG)) absorbed by the corresponding portions of the tissue, and hence improve diagnostic capabilities of the NIR imaging.

Aspects of the technology are described primarily in terms of an implementation using da Vinci® surgical systems developed by Intuitive Surgical, Inc. of Sunnyvale, California. Examples of such surgical systems are the da Vinci® Xi™ Surgical System (Model IS4000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems, e.g. the Model IS4000 are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices. While the technology is described primarily with reference to an example of a peer-in display, the technology may also be used in other types of wearable or non-wearable display devices such as a head-mounted display device used, for example, in virtual or augmented reality (VR/AR) systems. The images captured may also be displayed on a large format display such as a 3D TV like device or an image projected onto a screen of some kind and viewed by a user wearing glasses which complete the stereo effect by ensuring that the correct image goes to the correct eye. Alternatively, an auto-stereo type display may be used, for example a lenticular based LCD type of display that may also incorporate head and or eye tracking of the viewer (user).

Figure 1:
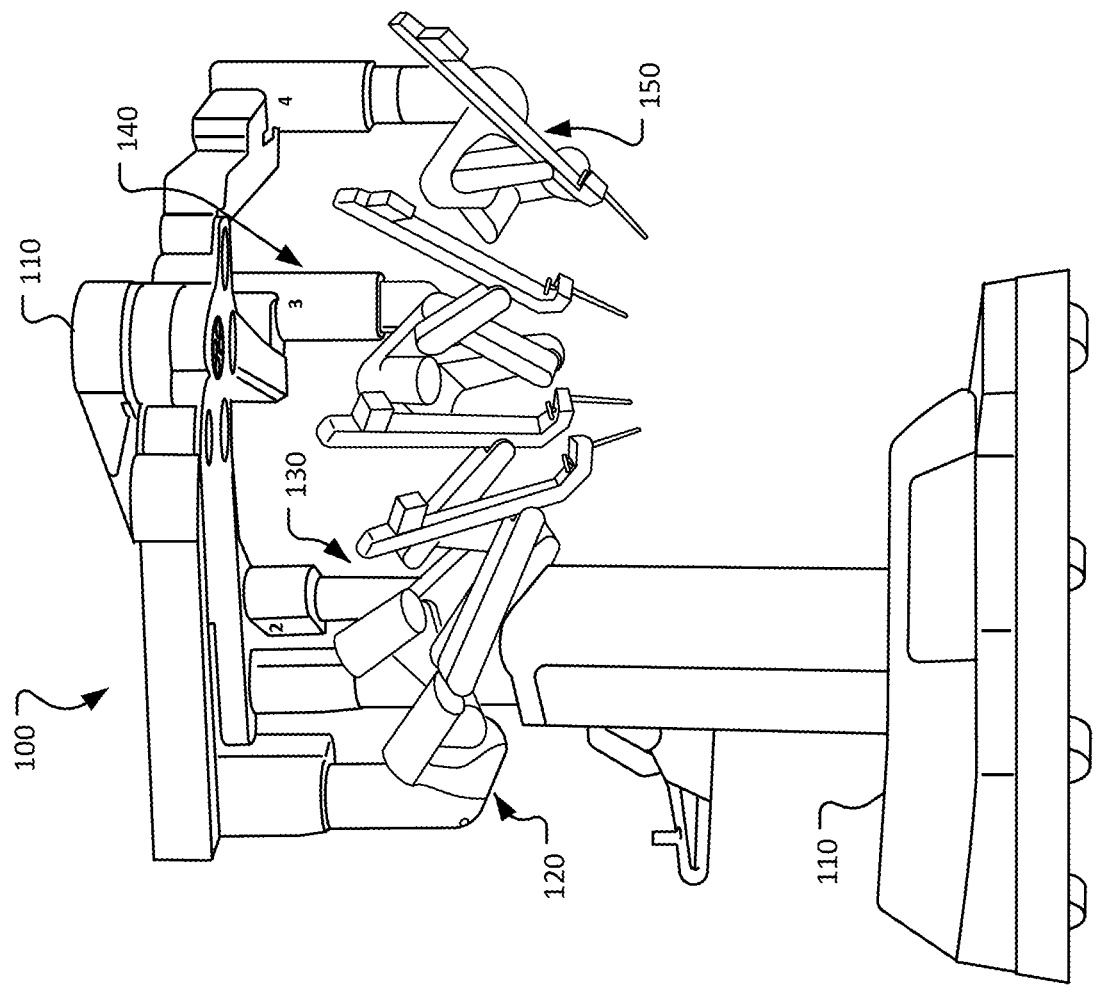
FIG. 1 is a perspective view of an example patient-side cart of a computer-assisted tele-operated surgery system.

Referring to FIGS. 1 and 2, systems for minimally invasive computer-assisted telesurgery (also referred to as MIS) can include a patient-side cart 100 and a surgeon console 50. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 50 includes a stereoscopic peer-in display 45 so that the user may view the surgical work site in stereo vision from images captured by the stereoscopic camera used in conjunction with the patient-side cart 100. Left and right eyepieces, 46 and 47, are provided in the stereoscopic peer-in display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 50 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 50 so the user may control movement and/or actuation of devices associated with the foot pedals.

A processing device 43 is provided in the surgeon console 50 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 50, the processing device 43 may also be distributed as subunits throughout the telesurgery system. One or more of the subunits may be physically remote (e.g., located on a remote server) to the telesurgery system.

Figure 3:
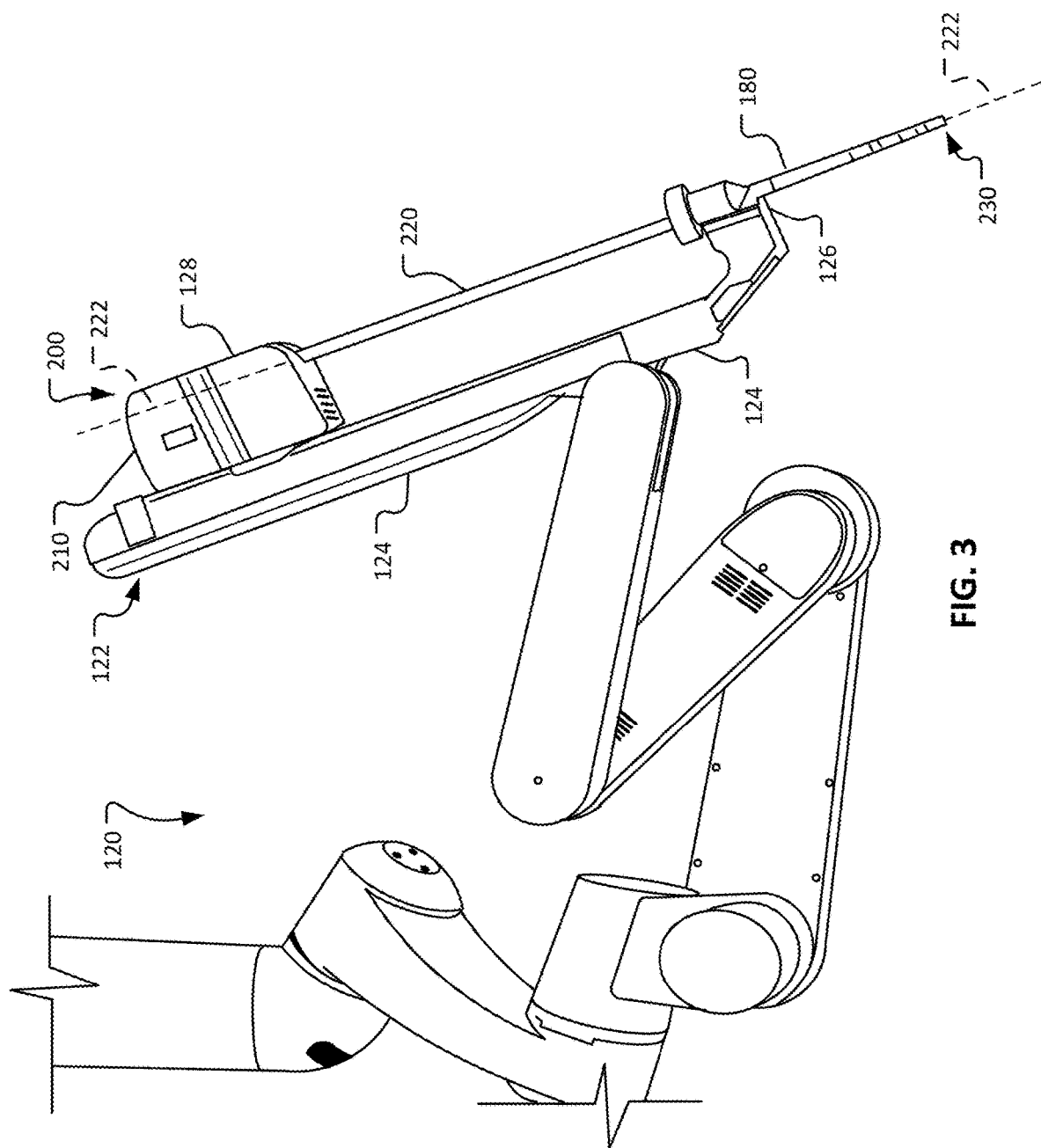
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as an endoscopic stereo camera and surgical instruments to perform minimally invasive surgery. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongated shaft 220 of the endoscopic camera (or endoscope) or surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 50 using the processing device 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processing device 43. The surgical instrument 200 includes a transmission assembly 210, the elongated shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongated shaft 220 of the surgical instrument 200 is moved along the longitudinal axis 222. In such a manner, the end effector 230 can be inserted and/or retracted from a surgical workspace within the body of a patient.

Laparoscopic surgery can entail the surgeon viewing the surgical site with the endoscope and performing fine motor manipulations with laparoscopic instruments for exploration, dissection, suturing, and other surgical tasks. These tasks often require fine bi-manual interactions with tissue. In some cases, such bi-manual motor tasks may generally be more easily performed when the surgeon is presented with a 3D view of the surgical scene. The surgical workspace within the body of a patient (the surgical scene) can be presented as a 3D visualization to the surgeon via the stereoscopic display 45. While the technology described herein primarily uses examples of a peer-in stereoscopic display, other types of stereoscopic and non-stereoscopic displays are also within the scope of the technology. A peer-in stereoscopic display refers to a display that allows a user to look into the display without having to wear it or simultaneously share it with another user. A stereo microscope can be an example of a peer-in stereoscopic display. The stereoscopic display 45, as illustrated in FIG. 2 is another example of a peer-in stereoscopic display.

Figure 4:
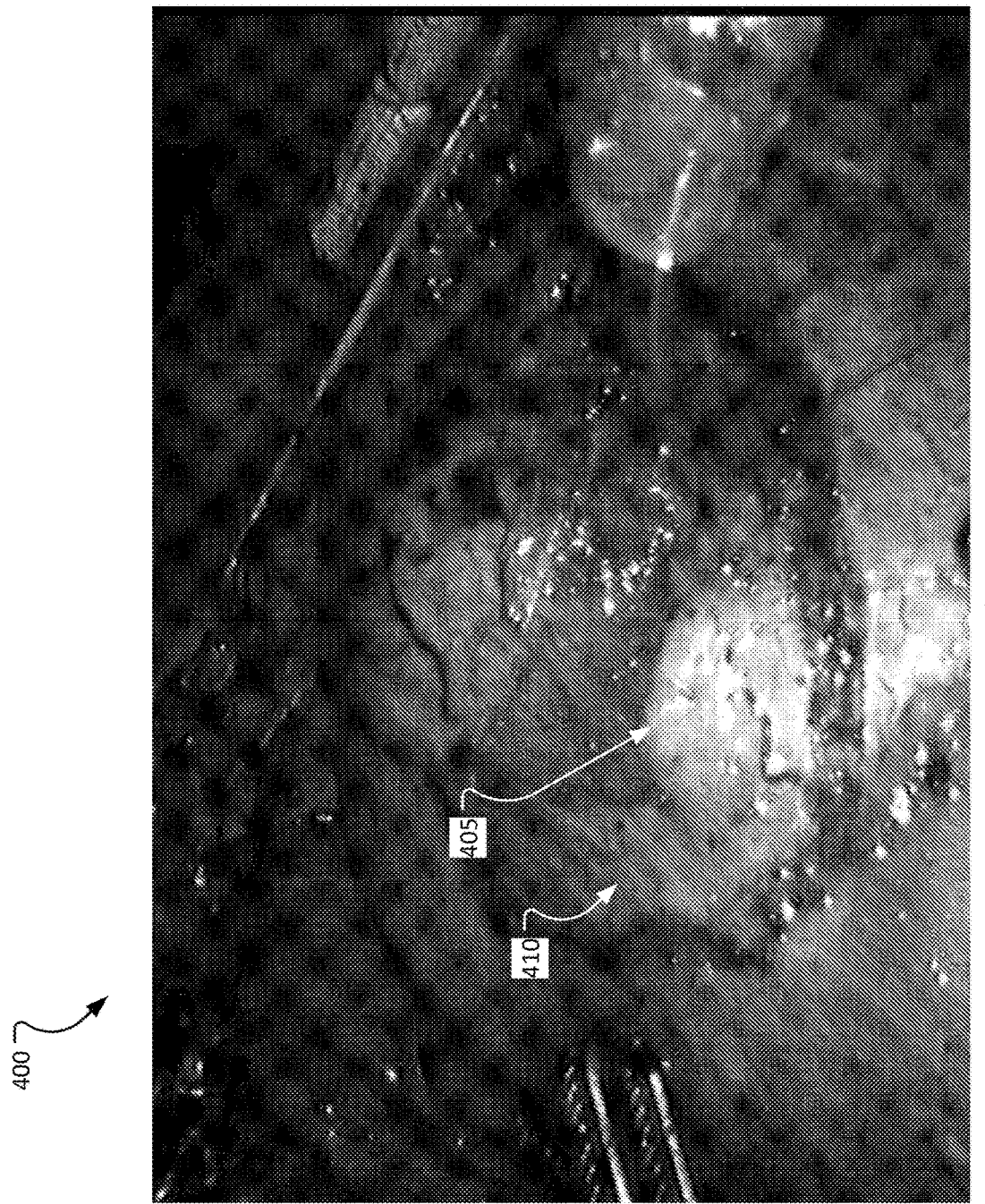
FIG. 4 is an example of a standard near-infrared (NIR) image.

In some implementations, the stereoscopic display 45 can be configured to present NIR images to a surgeon. For this, a dye such as ICG is administered to a patient or subject, and the locations of the dye is imaged under NIR excitation signals. Dyes such as ICG produces a fluorescence, which can be detected under NIR excitation. Presenting NIR images on a display can include generating an image of the corresponding surgical area, and overlaying on it a representation of the fluorescent signal produced by ICG. The image of the surgical area is displayed as a black-and-white image and the fluorescent signal is displayed typically in green on top of the black-and-white image. An example of such an NIR image 400 is illustrated in FIG. 4.

The intensity of the green fluorescent signal in an NIR image can be a function of various parameters. For example, in addition to being a function of the amount of ICG in the tissue, the intensity of the fluorescence is directly related to the amount of NIR light incident on the portion of the tissue where ICG is present. In the example of FIG. 4, the intensity of the fluorescent signal in the portion 405 is higher than that in the portion 410. However, at least a portion of the intensity variation may be attributable to the amount of NIR excitation energy incident on the corresponding portions. For example, the higher intensity in the portion 405 may be due to a higher amount of excitation energy incident on the portion 405 (as compared to that on the portion 410), and not necessarily because the amount of ICG in portion 405 is higher. Also, because the endoscope light source is typically located at the tip of the endoscope probe, the intensity of light or excitation energy affecting the ICG (and therefore the amount of fluorescence emitted from the corresponding tissue) is dependent on the endoscope position (e.g., distance from the tissue, angle, etc.). For example, if the intensity of the fluorescence is directly proportional to the amount of NIR that is incident on the ICG, the ICG in the center of the field-of-view (FOV) of the NIR source (where the NIR light is the brightest) will glow a bright green. However, if the same portion is moved to the side of the FOV, the fluorescence intensity diminishes significantly if the NIR light is not as intense at the edges of the FOV. Furthermore, if the endoscope is moved forward towards the tissue or backwards away from the tissue, the intensity of the fluorescence varies by increasing with forward motion and decreasing with backward motion.

In some cases, where the information gleaned from NIR Imaging is dependent primarily on the amount of ICG in the tissue, the variation in fluorescence due to the variation in the amount of excitation energy incident on the tissue is unwanted. The technology described herein describes using a reference NIR signal to compensate and correct for any endoscope position effects. Such positional independence can improve the diagnostic capabilities of the NIR imaging, for example, by making it easier for the surgeon to determine the quantity of ICG in a particular tissue type. In some cases, the improved visualization afforded by the technology described herein makes it easier to locate the margins of afflicted tissue (e.g., by detecting cancerous cells more accurately), thereby potentially improving the underlying surgical process.

Figure 5:
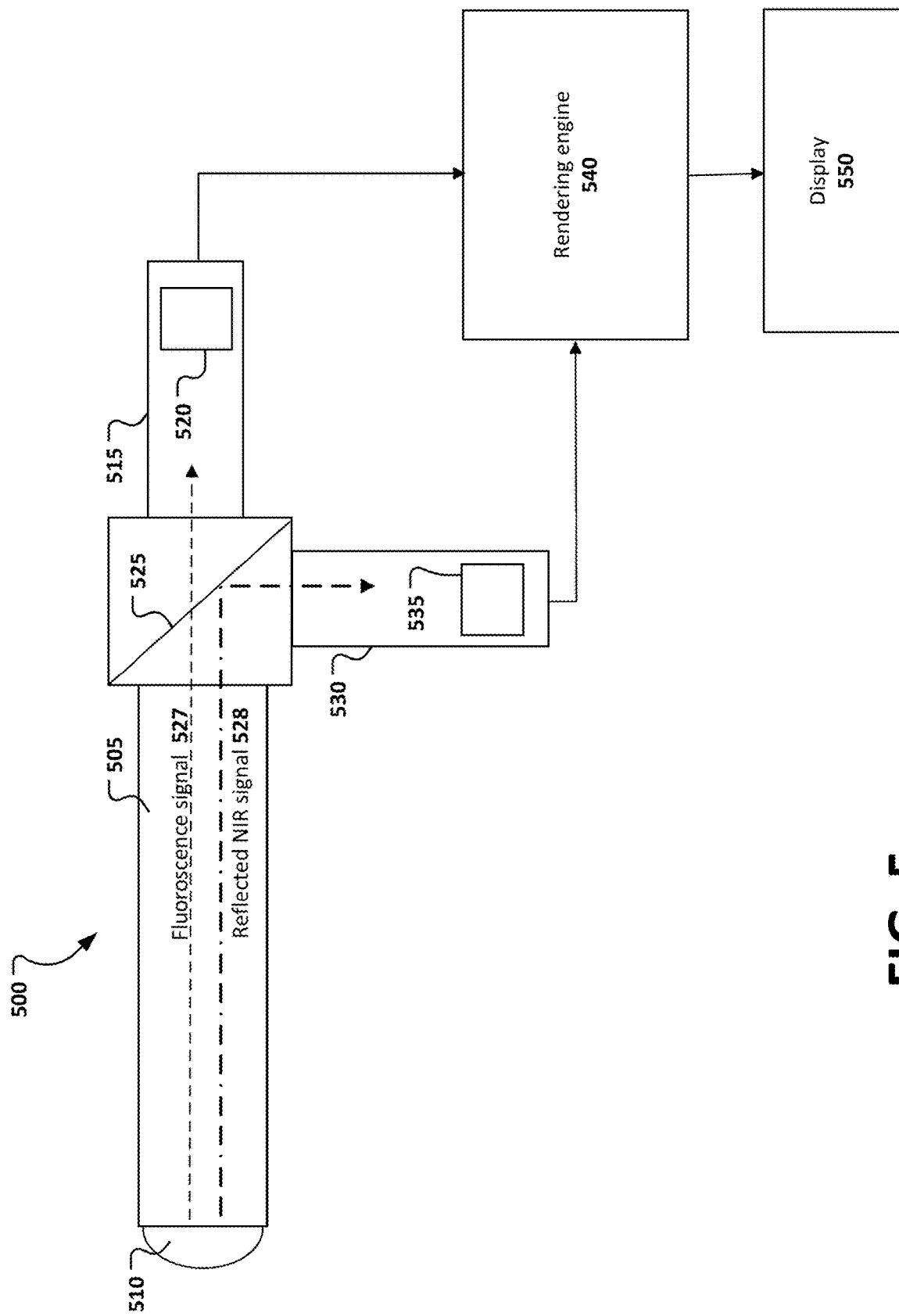
FIG. 5 is a block diagram of an example endoscopic system that implements the technology described herein.

FIG. 5 is a block diagram of an example endoscopic system 500 that implements the technology described herein. The system 500 includes an endoscope shaft 505 that is configured to be inserted in a human body. One or more illumination sources configured to emit excitation energy for illuminating tissues can be disposed at the tip 510 of the endoscope shaft 505. The one or more illumination sources can include NIR sources and/or sources configured to emit electromagnetic radiation in the visible range, and/or other wavelength ranges. In some implementations, the one or more The tip 510 and the shaft 505 can include various optical elements that direct light from tissues/surgical scenes through the shaft 505 towards one or more image sensors or cameras located at the opposite end of the shaft 505.

In some implementations, the system 500 includes a fluorescence detecting camera 515 that is configured to sense the fluorescence emanating from the tissue/surgical scene illuminated using the one or more illumination sources disposed at the tip 510. The fluorescence detecting camera 515 includes an image sensor 520 configured to sense electromagnetic energy in the wavelength range where the fluorescence signal is expected. For example, when ICG is used as a dye in NIR imaging, the expected fluorescence spectrum is about 750-950 nm. In such cases, the image sensor 520 can be configured to sense the fluorescence spectrum by disposing an optical filter before the image sensor 520 in the optical path, with a passband of the optical filter being in the 750-950 nm range. Other optical filters may be used depending on the dye and/or absorption/emission spectra associated with the tissue being imaged.

In some implementations, the wavelength range associated with the NIR excitation energy coincides with the fluorescence spectrum. For example, the NIR excitation energy can be provided via 800 nm electromagnetic radiation. Accordingly, the optical filter configured to pass signals in the fluorescence spectrum can be also be configured to include a stop band that reduces the effect of the NIR excitation energy on the output of the image sensor 520. Such filters absorb/block at least a portion of the NIR excitation energy that is reflected from the tissue.

The technology described herein stems, at least in part, from the realization that the NIR excitation energy reflected from a portion of the tissue can be used as a measure of the amount of excitation energy incident on that portion of the tissue. For example, assuming reflectance of the entire FOV to be uniform, the variation in the amount of excitation energy reflected from different portions of the FOV can be used as a measure of the amount of excitation energy incident on the corresponding portions. If the reflectance properties of the tissues in the FOV are known, appropriate corrections/adjustments can be incorporated to estimate the amount of excitation energy incident on the corresponding portions. In any case, the estimates of the amount of excitation energy incident at different portions of the FOV can be used to correct the sensor output of the image sensor 520 such that the corrected output is substantially independent of the variations due to the non-uniform distribution of the excitation energy. For example, if the estimated amount of excitation energy incident on a portion of the tissue is high, the corresponding portion of the output of the sensor 520 can be attenuated accordingly. On the other hand, if the estimated amount of excitation energy incident on a portion of the tissue is low, the corresponding portion of the output of the sensor 520 can be boosted accordingly. In some implementations, such correction can be represented using the following equation:

$$[\text{Absolute Fluorescence Signal}]=[\text{Sensed Fluorescence Signal}]/[\text{Estimated Excitation Signal}] \quad (1)$$

wherein Sensed Fluorescence Signal represents the output of the image sensor 520 for one or more pixels corresponding to a portion of the FOV, Estimated Excitation Signal represents the estimated amount of excitation energy incident on the corresponding portions of the FOV, and Absolute Fluorescence Signal represents the corrected signal.

The amount of excitation energy incident on different portions of the FOV can be determined in various ways. In some implementations, the amount of incident excitation energy can be sensed using one or more sensors. For example, as shown in FIG. 5, the system 500 can include a separate NIR camera 530 that includes an image sensor 535 for sensing NIR excitation energy. In such cases, the system 500 also includes a filter 525, which instead of absorbing/blocking the reflected NIR excitation energy, selectively reflects such energy towards the image sensor 535. The filter 525 can include a reflective surface that selectively reflects NIR excitation signals 528 m towards the image sensor 535 while allowing the fluorescence signals 527 to pass through towards the image sensor 520. In some implementations, other arrangements may be used. For example, the locations of the fluorescence detecting camera 515 and the NIR camera can be reversed, and the filter 525 can be configured to selectively reflect the fluorescence signals 527 while allowing the NIR excitation signals 528 to pass through. In any case, the fluorescence detecting camera 515 detects the fluorescence, and the NIR camera 530 detects the excitation energy reflected from the tissue such that the amount of excitation energy incident on the tissue can be estimated based on an output of the image sensor 535.

In some implementations, the amount of excitation energy incident on different portions of the FOV can be determined based on a model that represents the distribution/propagation pattern of electromagnetic energy from the one or more illumination sources disposed at the tip 510 of the endoscope shaft 505. For example, a theoretical/empirical model (e.g., a depth map) may provide information on how the intensity of the illumination falls off with distance/angle from the illumination source, and such a model may be used to determine the amount of excitation energy incident at a particular portion within the FOV. The model can be configured to, for example, account for the intensity variation due to the particular illumination pattern of the corresponding source, and/or the cosine factor fall-off in intensity. The endoscope system 500 can include a distance sensor (for example, a distance sensor disposed at the tip 510 of the endoscope shaft 505) for measuring/estimating a distance of the illumination source from the tissue in the FOV, and the distance information can be used to determine/estimate the amount of excitation energy incident on the various portions in the FOV.

The system 500 can include a rendering engine 540 that is configured to generate a corrected NIR image based on the sensor outputs received from the image sensors 520 and 535. The rendering engine can include one or more processing devices (e.g., the processing device 43 shown in FIG. 2) that can be configured to compute the Absolute Fluorescence signal for each pixel corresponding to the FOV in accordance with equation (1) above. In some implementations, with respect to pixels for which the estimated excitation signal is close to zero, the rendering engine 540 can be configured to mask the correction process in order to avoid any instability resulting from division by a near-zero value. The rendering engine 540 can then generate control signals for the display 550 such that the corrected NIR image is presented on the display 550. In some implementations, the display 550 can be disposed as a portion of the stereoscopic display 45 described above with reference to FIG. 1.

Figure 6:
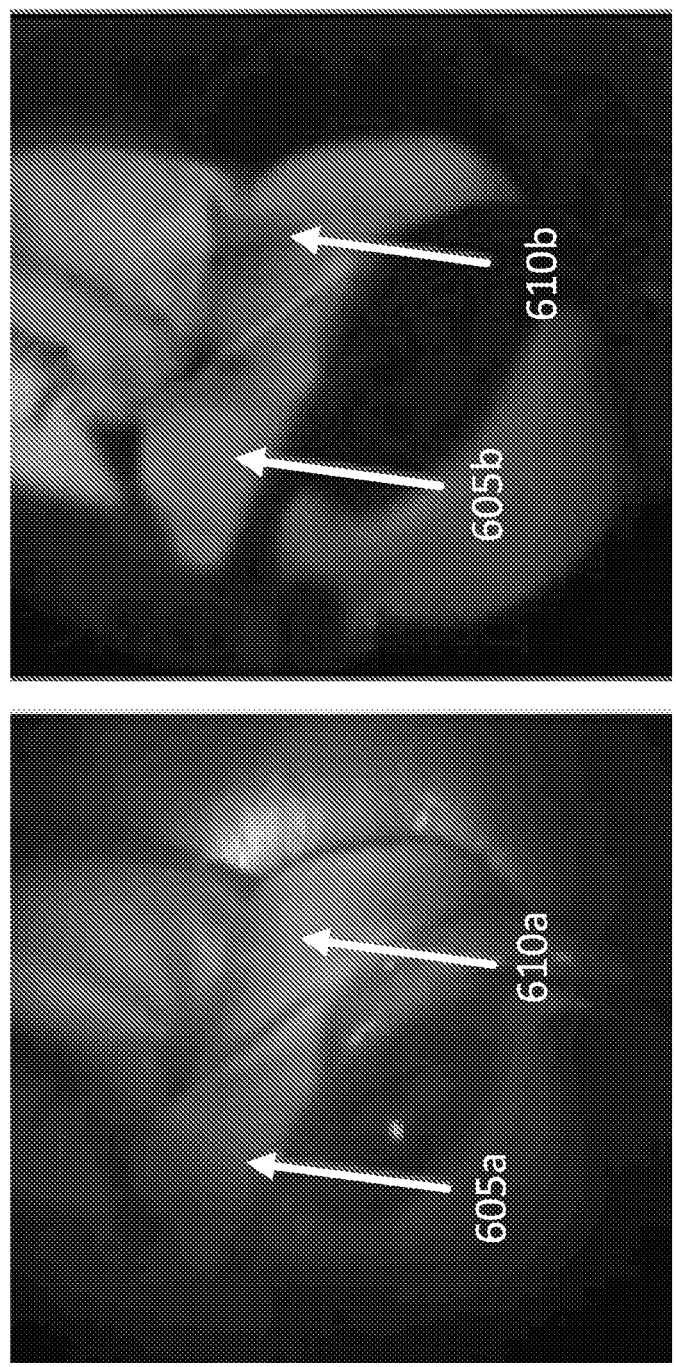
FIG. 6A is an example of a standard near-infrared (NIR) image.
FIG. 6B is an example of an NIR image generated in accordance with the technology described herein.

The normalization of NIR image pixel values with respect to corresponding estimates of incident excitation energy can provide several advantages. Some such advantages are illustrated in the examples of FIGS. 6A and 6B. Specifically, FIG. 6A is an example of a standard near-infrared (NIR) image without the corrections described herein, and FIG. 6B is an example of an NIR image generated in accordance with the technology described herein. In FIG. 6A, the intensity of the fluorescence in the region 605a is less than the intensity of the fluorescence in the region 610a. This may lead a surgeon or medical professional to believe that the amount of ICG in the region 610a is higher than the amount of ICG in the region 605a. However, as illustrated in FIG. 6B, upon correction of the NIR image in accordance with technology described herein, the opposite appears to be true. Specifically, in FIG. 6B, the region 610b appears to be darker than the region 605b, thereby indicating that the amount of ICG in the region 610b is less than the amount of ICG in the region 605b. The representation in FIG. 6A was therefore affected by the differential amount of incident excitation energy, which is accounted for in the corrected image of FIG. 6B.

As illustrated by the comparative examples of FIGS. 6A and 6B, the technology described herein can allow for visualization of the actual amount of dye such as ICG absorbed by various portions of the tissue. The examples shown in FIGS. 6A and 6B assumes that the absorbed ICG is at or near the surface of the tissue being visualized. In some implementations, additional corrections may be incorporated to account for ICG absorbed relatively deeper into the tissue. In some implementations, the capability to detect an actual amount of dye absorbed by the tissue facilitates various types of visualization associated with NIR imaging. For example, the data for the corrected NIR image can be used to demarcate different areas in accordance with the amount of dye absorbed. In some implementations, this can help the surgeon to better identify the contours of a diseased area. Referring back to FIG. 5, the rendering engine 540 can be configured, for example based on a user-input, to identify areas in an image where the ICG absorption is above a threshold value (e.g., 50%, 90%, or another percentage of the maximum absorption). The corresponding contours can then be presented on the display device 550. In some implementations, responsive to viewing the corrected NIR image and/or the above-described contours, a user-input from a surgeon can be received to operate a tele-operated surgical system such as the system shown in FIGS. 1 and 2.

Figure 7:
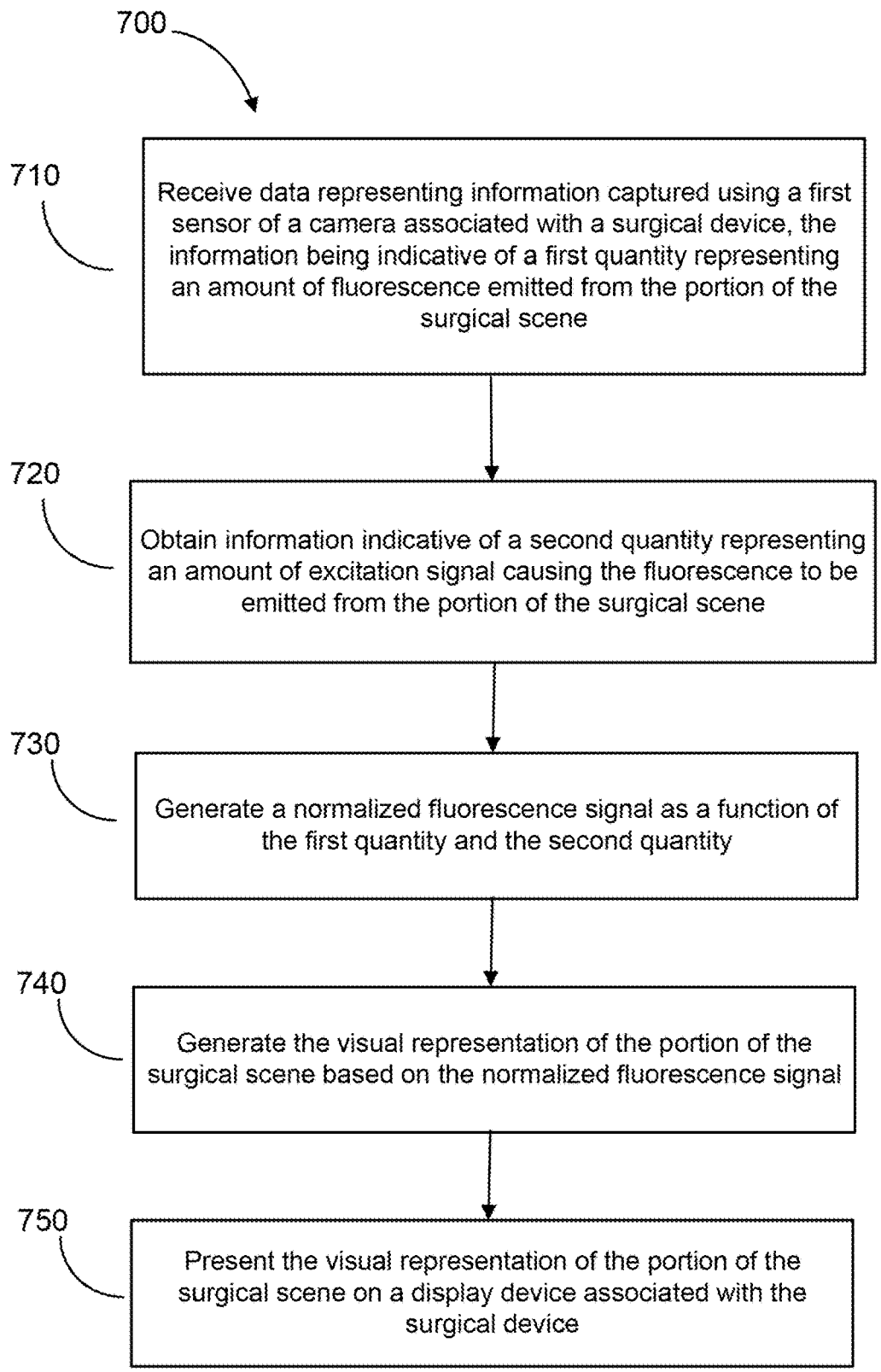
FIG. 7 is a flowchart of an example process for generating an NIR image in accordance with technology described herein.

FIG. 7 is a flowchart of an example process 700 for displaying a visual representation of a portion of a surgical scene on a display device. In some implementations, the display device can be the stereoscopic display 45 described above with reference to FIG. 2. In some implementations, at least a portion of the process 700 may be executed by the processing device 43 described above with reference to FIG. 2. Operations of the process 700 can include receiving data representing information captured using a first sensor of a camera associated with a surgical device (710). The information captured using the first sensor is indicative of a first quantity representing an amount of fluorescence emitted from the portion of the surgical scene. In some implementations, the camera can be an NIR camera disposed in an endoscope device. The fluorescence can occur when a dye (e.g., ICG) present in tissues at the surgical scene absorb excitation energy provided by a source (e.g., an NIR light source), and re-emits a portion of the absorbed energy in a different wavelength range. The wavelength range at which the reemission occurs can be referred to as the fluorescence spectrum.

Operations of the process 700 also includes obtaining information indicative of a second quantity representing an amount of excitation signal causing the fluorescence to be emitted from the portion of the surgical scene (720). In some implementations, the information indicative of the second quantity is obtained using a dual sensor system such as the endoscopic system illustrated in FIG. 5. For example, obtaining the information indicative of the second quantity can include receiving a portion of the excitation signal as reflected from the portion of the surgical scene, capturing the portion of the excitation signal using a second sensor such as the image sensor 535 of the NIR camera 530 shown in FIG. 5. The second quantity can then be determined based on an output signal from the second sensor. In some implementations, each of the first sensor and the second sensor can be a near-infrared (NIR) sensor. In some implementations, capturing the portion of the excitation signal includes changing a direction of propagation of the portion of the excitation signal towards the second sensor. This can be done, for example, using an optical filter 525 (FIG. 5) that includes a reflective surface or element disposed at an angle with respect to the initial direction of propagation the reflected NIR signal 528 (or the direction of propagation of the fluorescence signal 527).

In some implementations, obtaining the information indicative of the second quantity can also include accessing a depth map associated with a source of the excitation signal. Such a depth map can provide information on intensity variations of the excitation signal as a function of spatial separation from the source. In the implementations using such a depth map approach, data representing information about a spatial separation between the portion of the surgical scene and the source of the excitation signal may be received, and the second quantity can then be determined based on (i) the spatial separation between the portion of the surgical scene and the source, and (ii) information obtained from the depth map. The data representing information about the spatial separation can be received from a third sensor, such as a distance sensor disposed at the tip of an endoscope device. The information about the spatial separation between the portion of the surgical scene and the source can include an angle between the portion of the surgical scene and the source, and/or a distance between the portion of the surgical scene and the source.

Operations of the process 700 further include generating a normalized fluorescence signal as a function of the first quantity and the second quantity (730). In some implementations, the function of the first quantity and the second quantity can include a ratio of the first quantity to the second quantity, such as the ratio represented in the right-hand side of equation (1).

Operations of the process 700 also include generating the visual representation of the portion of the surgical scene based on the normalized fluorescence signal (740), and presenting the visual representation of the portion of the surgical scene on a display device associated with the surgical device (750). In some implementations, this can include receiving user-input on a threshold condition associated with the normalized fluorescence signal, determining regions where the normalized fluorescence signal satisfies the threshold condition, and generating the visual representation such that the visual representation includes identification of the regions where the normalized fluorescence signal satisfies the threshold condition. For example, a surgeon can provide a user-input requesting displaying the contours of the regions where the ICG absorption is above a threshold value, and the visual representation can then include such contours accordingly. In some implementations, responsive to presenting the visual representation of the surgical scene on the display device, user-input pertaining to operating the surgical device at the surgical scene can be received.

The functionality of the tele-operated surgery system described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on what may be claimed, but rather as descriptions of features that may be specific to particular embodiments. Other embodiments may also be within the scope of the technology described herein. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A method of displaying a visual representation of a portion of a surgical scene, the method comprising:
   receiving data representing information captured using a first sensor of a camera associated with a surgical device, the information being indicative of a first quantity representing an amount of fluorescence emitted from the portion of the surgical scene;

obtaining information indicative of a second quantity representing an amount of excitation signal causing the fluorescence to be emitted from the portion of the surgical scene;

generating, by one or more processing devices, a normalized fluorescence signal as a function of the first quantity and the second quantity;

generating the visual representation of the portion of the surgical scene based on the normalized fluorescence signal; and presenting the visual representation of the portion of the surgical scene on a display device associated with the surgical device, wherein obtaining the information indicative of the second quantity comprises:

accessing a depth map associated with a source of the excitation signal, the depth map providing information on intensity variations of the excitation signal as a function of spatial separation from the source;

receiving data representing information about a spatial separation between a surface of the portion of the surgical scene and the source of the excitation signal; and determining the second quantity based on (i) the spatial separation between the surface of the portion of the surgical scene and the source, and (ii) the depth map.

2. The method of claim 1, wherein obtaining the information indicative of the second quantity comprises:

receiving a portion of the excitation signal as reflected from the surface of the portion of the surgical scene;

capturing the portion of the excitation signal using a second sensor; and determining the second quantity based on an output signal from the second sensor.

3. The method of claim 2, wherein each of the first sensor and the second sensor is a near-infrared (NIR) sensor.

4. The method of claim 2, wherein capturing the portion of the excitation signal further comprises:

changing a direction of propagation of the portion of the excitation signal towards the second sensor.

5. The method of claim 1, wherein the information about the spatial separation between the surface of the portion of the surgical scene and the source comprises at least one of (i) an angle between the surface of the portion of the surgical scene and the source, or (ii) a distance between the surface of the portion of the surgical scene and the source.

6. The method of claim 1, wherein presenting the visual representation comprises:

receiving user-input on a threshold condition associated with the normalized fluorescence signal;

determining regions where the normalized fluorescence signal satisfies the threshold condition; and generating the visual representation such that the visual representation includes identification of the regions where the normalized fluorescence signal satisfies the threshold condition.

7. The method of claim 1, further comprising receiving user input responsive to presenting the visual representation of the surgical scene on the display device, wherein the user input pertains to operating the surgical device at the surgical scene.

8. The method of claim 1, wherein the function of the first quantity and the second quantity comprises a ratio of the first quantity to the second quantity.

9. The method of claim 1, wherein the excitation signal is emitted from a distal end of an endoscope that includes the first sensor.

10. The method of claim 1, wherein the data representing information about the spatial separation is received from a distance sensor positioned at a distal end of an endoscope that includes the first sensor.

* * * * *